United States Patent [19]

Alon

[11] Patent Number: 5,230,703
[45] Date of Patent: Jul. 27, 1993

[54] WOUND INFECTION RESOLUTION UTILIZING ANTIBIOTIC AGENTS AND ELECTRICAL STIMULATION

[75] Inventor: Gad Alon, Rockville, Md.

[73] Assignee: Staodyn, Inc., Longmont, Colo.

[21] Appl. No.: 865,473

[22] Filed: Apr. 9, 1992

[51] Int. Cl.⁵ .............................................. A61N 1/30
[52] U.S. Cl. ...................................... 604/20; 128/898
[58] Field of Search ............... 128/798, 802, 803, 898; 604/20, 49

[56] References Cited

U.S. PATENT DOCUMENTS

| | | | |
|---|---|---|---|
| 2,493,155 | 1/1950 | McMillan | 604/20 |
| 3,964,477 | 6/1976 | Ellis et al. | 604/20 |
| 4,141,359 | 2/1979 | Jacobsen et al. | 604/20 |
| 4,465,582 | 9/1979 | Sibalis | 604/20 |
| 4,640,689 | 2/1987 | Sibalis | 604/20 |
| 4,702,732 | 10/1987 | Powers et al. | 604/20 |
| 4,767,401 | 8/1988 | Seiderman | 604/20 |
| 4,786,277 | 11/1988 | Powers et al. | 604/20 |
| 4,808,152 | 2/1989 | Sibalis | 604/20 |
| 4,846,181 | 7/1989 | Miller | 128/802 |
| 4,850,956 | 7/1989 | Bontemps | |
| 4,883,457 | 11/1989 | Sibalis | 604/20 |
| 4,895,154 | 1/1990 | Bartelt et al. | |
| 4,921,475 | 5/1990 | Sibalis | 604/20 |
| 4,931,046 | 6/1990 | Newman | 604/20 |
| 4,942,883 | 7/1990 | Newman | 604/20 |
| 5,042,975 | 8/1991 | Chien et al. | 604/20 |
| 5,147,297 | 9/1992 | Myers et al. | 604/20 |

*Primary Examiner*—Stephen C. Pellegrino
*Assistant Examiner*—Michael Rafa
*Attorney, Agent, or Firm*—Robert E. Harris

[57] ABSTRACT

A method is disclosed for promoting resolution of infection at an externally accessible wound site, such as a skin tear or ulcer, of a patient using antibiotic agents (normally comprising one or more antibiotic drugs) in combination with electrical stimulation. The antibiotic agents administered to the patient enter the blood stream of the patient, and the electrical stimulation is applied, while the antibiotic agents are in the blood stream, to the patient through one or more active electrodes to cause increased circulation of blood to the wound site to thereby enhance resolution of the infection at the wound site.

16 Claims, No Drawings

WOUND INFECTION RESOLUTION UTILIZING ANTIBIOTIC AGENTS AND ELECTRICAL STIMULATION

FIELD OF THE INVENTION

This invention relates to resolution of infection at a wound site, and, more particularly, relates to resolution of infection at an externally accessible wound site using a combination of antibiotic agents and electrical stimulation.

BACKGROUND OF THE INVENTION

Antibiotic agents are well known that are capable of entering the blood stream to fight infection, including bacterial infection, in a living body, and such use of antibiotic agents is known to include treatment for externally accessible soft tissue wounds, including skin tears and ulcers, for example, located on, or adjacent to the skin of the living body.

It is also now known that healing of soft tissue wounds can be enhanced by use of electrical stimulation applied to the wound (see, for example, U.S. Pat. No. 4,846,181).

It has also been heretofore suggested that iontophoresis can be used to treat a wound by driving a drug through the skin of a living body using a DC electrical signal (see, for example, U.S. Pat. Nos. 4,141,359, 4,460,689, 4,808,152, 4,865,582, 4,883,457, 4,921,475 and 4,931,046), and it has been heretofore suggested that an AC signal can be applied to a living body for pain suppression through the same electrode that is utilized to provide the DC signal to drive the drug into the body (see, for example, U.S. Pat. Nos. 4,702,732 and 4,786,277).

Thus, while the now known prior art shows the use of antibiotic agents capable of entering the blood stream to fight infection, as well as showing the use of electrical signals to promote healing of soft tissue wounds or to drive a drug into a wound, there is no apparent showing of treating a wound using antibiotic agents in combination with electrical stimulation to cause increased blood circulation at the infected wound site while the antibiotic agents are in the blood stream and thereby enhance resolution of infection at the wound site.

SUMMARY OF THE INVENTION

This invention provides a method for treating infection at an externally accessible wound site on a living body by applying electrical stimulation while antibiotic agents are in the blood stream of the living body to cause increased circulation of the blood at the wound site and thereby promote resolution of infection at the wound site.

It is an object of this invention to provide a novel method for treating infection at an externally accessible wound site.

It is another object of this invention to provide a novel method for treating infection at an externally accessible wound site utilizing a combination of antibiotic agents and electrical stimulation.

It is still another object of this invention to provide a novel method of providing accelerated resolution of infection at a soft tissue wound site of a patient by applying electrical stimulation, while antibiotic agents are in the blood stream of the patient, to the patient to cause increased circulation of blood to the wound site and thereby enhance resolution of infection at the wound site.

With these and other objects in view, which will become apparent to one skilled in the art as the description proceeds, this invention resides in the novel method substantially as hereinafter described, and more particularly defined by the appended claims, it being understood that changes in the precise embodiment of the herein disclosed invention are meant to be included as come within the scope of the claims.

DESCRIPTION OF THE INVENTION

In this invention, antibiotic agents (normally comprising one or more antibiotic drugs) are conventionally administered to a living body, or patient, normally either by intramuscular injection (as, for example, by inserting an antibiotic drug through a needle into the arm or thigh muscle), orally (as, for example, by causing the antibiotic drug to be ingested), intravenously (as, for example, by insertion through an intravenous drip), or topically (as, for example, by applying the antibiotic agents onto the wound site).

The administered antibiotic agents must be of sufficient strength to adequately fight the infection (such as bacterial infection) at the wound site (an externally accessible wound site, such as, for example, at a skin tear or ulcer). The antibiotic agents may be, for example, one or more of penicillin and clindamycin, and may be administered, for example, in doses of two million units where the infection at the wound site is streptococcus and/or staphylococcus.

By way of further example (and not by way of limitation), for oral administration, oxacillin may be utilized in a dosage of 50 mg/Kg/day every six hours (child) or 0.5–0.75 g every four to six hours (adult), clindamycin (non-penicillin) may be utilized in a dosage of 150–300 mg every six hours, erythromycin (non-penicillin) may be utilized in a dosage of 0.25–0.5 g every six hours, or penicillin may be utilized in a dosage of 600,000–2 million units every four to six hours; for intravenous administration, nafcillin may be utilized in a dosage of 1.5–2 g every four to six hours; for topical application, bacitracin-neomycin-polymyxin, mupirocin, cefoxitin or clindamycin may be utilized; and for oral administration, rifampin may be utilized in a dosage of 600 mg daily, cloxacillin may be utilized in a dosage of 500 mg four times daily, or ciprofloxacin could also be utilized.

The electrical stimulation must be such that microcirculation of the blood (at least at the margin of the wound) is enhanced at the externally accessible wound site. The increased blood circulation at the wound site is thought to be due to interstitial intermittent pressure when low level muscular stimulation is applied, or to vasodialtory reflex when the sensory nerves are stimulated. It has been found that healing is retarded, or even prevented, when blood circulation is reduced, or inhibited, and this is particularly true for chronic wounds (which, by definition, have reduced or compromised blood circulation). By increasing the blood circulation, however, chronic wounds can be made to act as "normal" wounds so that the rate of healing is more rapid.

Pulsed current or alternating current stimulation, such as provided, for example, by a transcutaneous electrical nerve stimulating (TENS) unit, has been found to be effective in increasing blood circulation at an externally accessible wound site. Such a unit normally supplies a monophasic or a biphasic pulsed electrical signal, an alternating current, or a direct current to improve, or increase, blood circulation at the externally accessible wound site (such a stimulator is suggested, for example, in U.S. Pat. No. 4,895,154).

The current providing enhanced blood circulation is applied directly to the wound site to be treated or is applied at a point away from the wound site (so long as circulation of the blood to the wound site is enhanced) through one or more active electrodes while the return electrode is placed at a distance from the wound site, as, for example, by placing the return electrode on the back of the thigh or leg for a wound in the lower leg.

In operation, the antibiotic agents are administered to the patient (i.e., the living body) about 10 to 60 minutes before the electrical treatment so that the antibiotic agents are in the blood stream during the ensuing electrical treatment. The current is then applied through the active electrode, or electrodes, so that blood circulation is enhanced at the wound site while the antibiotic agents are in the blood stream.

It is felt that if electrical stimulation causing increased blood circulation is applied while antibiotic agents are in the blood stream, this promotes transportation of the antibiotic agents to the wound site, and it has been observed that application of electrical stimulation while antibiotic agents are in the blood stream causes faster resolution of infection at the wound site. Specifically, it was shown in a pilot study that four diahletic ulcers that became infected and caused a rise in body temperature to over 102 degrees (°F.), redness of the entire foot, and marked swelling of the foot and over the ankle, were treated with combinations of antibiotics and electrical stimulation which resolved completely the above signs in three days. This represented only one-third of the time usually required for such resolution if only antibiotics are given.

It is felt that application of the electrical treatment for 30 to 45 minutes repeated twice daily will be effective for accomplishing faster resolution of infection when combined with application of antibiotic agents as set forth herein. It is also felt that the method of this invention is particularly useful for treating chronic or acute wounds, but is not meant to be restricted thereto.

In view of the foregoing, it can be appreciated that the method of this invention provides improved resolution of infections at an externally accessible wound site.

What is claimed is:

1. A method for promoting resolution of infection at an externally accessible wound site on a living body, said method comprising:
   administering antibiotic agents to a living body having an externally accessible wound site, said antibiotic agents being such that said antibiotic agents enter the blood stream of the living body;
   allowing sufficient time to elapse after administration of said antibiotic agents to insure that said antibiotic agents are in the blood stream of the living body; and
   after said sufficient time has elapsed to insure that said administered antibiotic agents are in the blood stream of the living body, applying electrical stimulation to said wound site while said antibiotic agents are in the blood stream of said living body to increase blood circulation at the wound site and thereby enhance healing resolution of infection at the wound site.

2. The method of claim 1 wherein said antibiotic agents are administered at a location spaced from said wound site.

3. The method of claim 2 wherein said antibiotic agents are administered by one of intramuscular injection, orally, intravenously and topically.

4. The method of claim 1 wherein said antibiotic agents are selected from the group consisting of oxacillin, clindamycin, erythromycin, penicillin, nafcillin, bacitracin-neomycin-polymyxin, mupirocin, cefoxitin, clindamycin, rifampin, cloxacillin, and ciprofloxacin.

5. The method of claim 1 wherein said electrical stimulation is applied as one of pulsed, alternating and DC current.

6. The method of claim 1 wherein said electrical stimulation is applied by use of an electrical unit having at least one active electrode positioned such that enhanced blood circulation occurs at said wound site.

7. The method of claim 6 wherein said electrical unit is a transcutaneous electrical stimulating unit.

8. The method of claim 6 wherein said electrical unit applies one of pulsed alternating and DC current.

9. The method of claim 1 wherein said wound to be treated is one of a chronic wound and an acute wound.

10. A method for promoting resolution of infection at an externally accessible wound site on a living body, said method comprising:
    administering antibiotic agents to a living body having an externally accessible infected wound site at a location spaced from said wound site with said antibiotic agents being such that said antibiotic agents enter the blood stream of said living body;
    allowing sufficient time to elapse after administration of said antibiotic agents to insure that said antibiotic agents are in the blood stream of the living body;
    providing an electrical unit capable of providing electrical current through at least one active electrode;
    placing said active electrode on said living body at a position such that blood circulation will be enhanced at said wound site at least while said electrical current is being supplied to said living body; and
    after said sufficient time has elapsed to insure that said administered antibiotic agents are in the blood stream of the living body, applying electrical current to said living body through said active electrode while said antibiotic agents are in the blood stream of said living body to increase blood flow to said wound site and thereby enhance resolution of infection at said wound site.

11. The method of claim 10 wherein said antibiotic agents are applied by one of a intramuscular injection, orally, intravenously, and topically.

12. The method of claim 10 wherein said antibiotics are selected from the group consisting of oxacillin, clindamycin, erythromycin, and penicillin when applied by intramuscular injection, nafcillin when applied intravenously, bacitracin-neomycin-polymyxin, mupirocin, cefoxitin and clindamycin when applied topically, and rifampin, cloxacillin and ciprofloxacin when applied orally.

13. The method of claim 10 wherein said electrical unit is a transcutaneous electrical stimulating unit.

14. The method of claim 10 wherein said electrical unit provides at least one of pulses, alternating current, and direct current.

15. The method of claim 10 wherein said wound site is one of a chronic wound and an acute wound.

16. A method for promoting resolution of infection at an externally accessible soft tissue wound site on a living body, said method comprising:

administering antibiotic agents to a living body by one of intramuscular injection, orally, intravenously and topically and in a dosage sufficient to adequately fight infection at said soft tissue wound site, said antibiotic agents being such that said antibiotic agents enter the blood stream of the living body no later than about ten to sixth minutes after being administered;

allowing sufficient time to elapse after administration of said antibiotic agents to insure that said antibiotic agents are in the blood stream of the living body;

providing a transcutaneous electrical stimulating unit providing an electrical current output through at least one active electrode;

placing said active electrode on said living body at a location such that blood circulation is enhanced when said electrical current is applied to said living body and placing a return electrode at a location spaced from the soft tissue wound site; and after said sufficient time has elapsed to insure that said administered antibiotic agents is in the blood stream of the living body, applying electrical current output to said living body through said active electrode while said antibiotic agents are in the blood stream of the living body to promote circulation of the blood at the soft tissue wound site to thereby increase resolution of infection at the wound site.

* * * * *